United States Patent

Hässig

Patent Number: 4,997,967
Date of Patent: Mar. 5, 1991

[54] PROCESS FOR THE PREPARATION OF ISOTHIOCYANATES

[75] Inventor: Robert Hässig, Gipf-Oberfrick, Switzerland

[73] Assignee: Ciba-Geigy Corporation, Ardsley, N.Y.

[21] Appl. No.: 458,124

[22] Filed: Dec. 28, 1989

[51] Int. Cl.$^5$ .......................................... C07C 331/00
[52] U.S. Cl. .................................................... 558/19
[58] Field of Search ......................................... 558/19

[56] References Cited

PUBLICATIONS

Liquid-Liquid Equilibrium Data Collection, Sorensen, et al. (1979), Schön & Wetzel GmbH, pp. 482–487.

Primary Examiner—Mary C. Lee
Assistant Examiner—Robert C. Whittenbaugh
Attorney, Agent, or Firm—Edward McC. Roberts

[57] ABSTRACT

There is disclosed a process for the preparation of isothiocyanates of formula

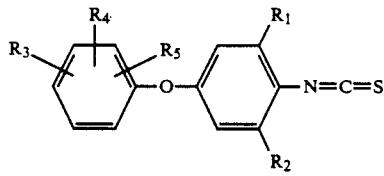

wherein $R_1$ and $R_2$ are each independently of the other $C_1$-$C_6$alkyl and $R_3$, $R_4$ and $R_5$ are each independently of the other hydrogen, halogen, $C_1$-$C_4$alkyl, $C_1$-$C_4$alkoxy, trifluoromethyl or nitro, which process comprises an amine of formula

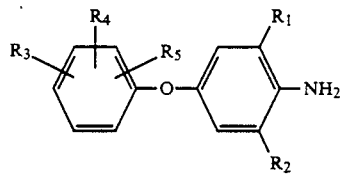

with ammonium thiocyanate or an alkali metal thiocyanate, in the presence of acid and an inert solvent, to the thiourea of formula

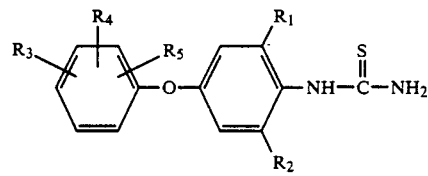

and cleaving said thiourea by heating. The essential feature of this process consists in carrying out the reaction of the amine of the above formula with ammonium thiocyanate or an alkali metal thiocyanate in the presence of 0.5-5% by weight of water, based on the total weight of the reaction mixture.

The isothiocyanates of the above formula are intermediates for the synthesis of pesticidal compounds.

20 Claims, No Drawings

PROCESS FOR THE PREPARATION OF ISOTHIOCYANATES

The present invention relates to a process for the preparation of isothiocyanates of formula I

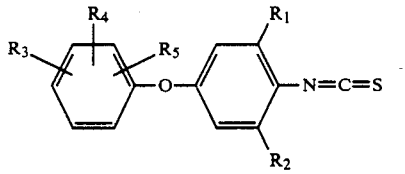

wherein $R_1$ and $R_2$ are each independently of the other $C_1$-$C_6$alkyl and $R_3$, $R_4$ and $R_5$ are each independently of the other hydrogen, halogen, $C_1$-$C_4$alkyl, $C_1$-$C_4$alkoxy, trifluoromethyl or nitro, The isothiocyanates of formula I are useful intermediates for the synthesis of pesticidal compounds. For example, they may be converted by reaction with mono- or dialkylamines and further optional reaction with alkyl halides into the corresponding 1,3-disubstituted thioureas or isothioureas which have pronounced insecticidal and acaricidal activity. Such insecticidal and acaricidal compounds, and the preparation and use thereof, are disclosed, for example, in German Offenlegungsschrift No. 3 034 905.

It is known to prepare isothiocyanates by reacting primary amines with thiophosgene [q.v. Houben-Weyl, Methoden der organischen Chemie, IX, 875 (1955)]. Although isothiocyanates can normally be obtained in this manner in very good yield, the method is unfavourable for an economic preparation of isothiocyanates on an industrial scale because of the high cost of thiophosgene and the difficulty of handling it.

It is further known to react primary amines, especially primary aromatic amines, in the form of their salts, in an inert solvent, with ammonium thiocyanates or alkali metal thiocyanates to the corresponding asymmetrically substituted thioureas [q.v. Houben-Weyl), Methoden der organischen Chemie, IX, 888 (1955)], and to convert these thioureas into the corresponding isothiocyanates by splitting off ammonia [q.v. Chemistry and Industry, 27, 785 (1954)]. Although the combination of these known process steps avoids the drawbacks involved in the use of thiophosgene, the thiourea is none the less still obtained in unsatisfactory yield even when using aromatic amines.

It is therefore the object of the present invention to provide a process for the preparation of isothiocyanates of formula I starting from readily accessible and cheap intermediates which are easy to handle, which process makes it possible to prepare the isothiocyanates of formula I in simple manner and in good yield.

It has been found that the reaction of the amines from which the isothiocyanates of formula I are derived with ammonium thiocyanates or alkali metal thiocyanates proceeds almost quantitatively to the corresponding thioureas by carrying out this reaction in an inert solvent in the presence of 0.5-5% by weight of water, based on the total weight of the reaction mixture.

Accordingly, the process of the present invention for the preparation of isothicyanates of formula I comprises reacting an amine of formula II

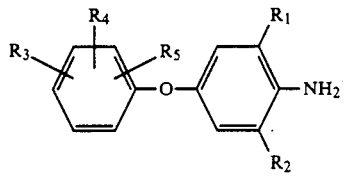

wherein $R_1$, $R_2$, $R_3$, $R_4$ and $R_5$ are as defined for formula I, in the presence of at least the equivalent amount of an acid and in the presence of 0.5-5% by water, based on the total weight of the reaction mixture, in an inert solvent, with ammonium thiocyanate or an alkali metal thiocyanate to a thiourea of formula III

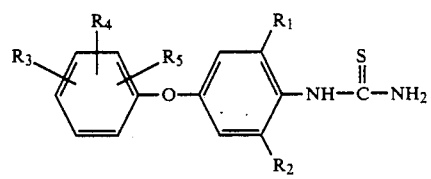

wherein $R_1$, $R_2$, $R_3$, $R_4$ and $R_5$ are as defined for formula I, and cleaving said thiourea by heating to give an isothiocyanate and ammonia.

Among the isothiocyanates of formula I obtainable by the process of this invention, those are preferred in which $R_1$ and $R_2$ are each independently of the other $C_2$-$C_4$alkyl, preferably ethyl, n-propyl, isopropyl, n-butyl, isobutyl, sec-butyl or tert-butyl, $R_3$ is hydrogen, chloro, methoxy, trifluoromethyl or nitro, and $R_4$ and $R_5$ are each hydrogen or chloro. Particularly preferred isothiocyanates of formula I are those wherein $R_1$ and $R_2$ are each isopropyl or sec-butyl, and $R_3$ is hydrogen, chloro or trifluoromethyl, and $R_5$ is hydrogen. The most preferred compound is 2,6-diisopropyl-4-phenoxyphenylisothiocyanate.

Suitable acids in the presence of which the reaction of the amines of formula II with ammonium thiocyanate or an alkali metal thiocyanate can be carried out are normally strong, non-oxidising mineral acids. Preferred acids are hydrochloric acid, hydrobromic acid and sulfuric acid. Hydrochloric acid is especially preferred. The acids can be used in stoichiometric amount or in excess. The molar ratio of amine of formula II to acid is conveniently from 1:1 to 1:1.25. The preferred molar ratio of amine of formula II to acid is 1:1 to 1:1.15.

The amines of formula II are preferably used in the form of their salts, most preferably in the form of their hydrochlorides.

It is preferred to carry out the reaction of the amines of formula II in an inert, water-immiscible organic solvent. Suitable solvents are aromatic hydrocarbons, preferably alkylbenzenes or mixtures of alkylbenzenes having a boiling range from 110° to 170° C., such as toluene, ethyl benzene, xylenes, cumene or trimethylbenzenes, or mixtures of such alkylbenzenes. Further suitable solvents are aliphatic and aromatic halogenated hydrocarbons such as methylene chloride, chloroform, carbon tetrachloride, 1,2-dichloroethane, chlorobenzene and o-dichlorobenzene. Preferred solvents are toluene and xylenes, as well as mixtures of alkylbenzenes. Particularly preferred solvents are xylenes and mixtures of alkylbenzenes having a boiling range from 110° to 170° C. Particularly suitable mixtures of alkylbenzenes are the mixtures obtainable under the registered trademark Solvesso ® 100 (Esso) and Shellsol ® A (Shell) having a boiling range from 150° to 170° C.

The amount of water in the presence of which the reaction of the amine of formula II with the ammonium thiocyanate or alkali metal thiocyanate is carried out is preferably 1–2% by weight, based on the total weight of the reaction mixture.

Particularly suitable alkali metal thiocyanates are sodium and potassium thiocyanate. It is preferred to use sodium thiocyanate. The ammonium thiocyanate or alkali metal thiocyanate can be used in stoichiometric amount. It is preferred, however, to use 1.05 to 1.25 mol of ammonium thiocyanate or alkali metal thiocyanate per mol of amine of formula II.

The reaction of the amine of formula II with the ammonium thiocyanate or alkali metal thiocyanate is conveniently carried out in the temperature range from 80° to 120° C. Preferably the reaction of the amine of formula II with the ammonium thiocyanate or alkali metal thiocyanate is carried out in the temperature range from 90° to 110° C.

The cleavage of the thiourea of formula III is conveniently carried out in the temperature range from 125° to 170° C., preferably from 140° to 160° C., in an inert solvent. Suitable solvents in which the cleavage of the thioureas of formula III can be carried out are aromatic hydrocarbons, preferably alkylbenzenes or mixtures thereof having a boiling range from 125° to 170° C., such as ethyl benzene, xylenes, trimethylbenzenes, ethyl methyl benzenes and cumene, as well as mixtures of such alkylbenzenes. Further suitable solvents for the thermal cleavage of the ureas of formula III are aromatic halogenated hydrocarbons such as chlorobenzene and o-dichlorobenzene. Preferred solvents in which the cleavage of the thioureas of formula III can be carried out are chlorobenzene, xylenes, as well as mixtures of alkylbenzenes, for example the mixtures obtainable under the registered trademark Solvesso ® 100 (Esso) and Shellsol ® A (Shell) having a boiling range from 150° to 170° C. Depending on the reaction temperature, the cleavage reaction takes from 3 to 6 hours.

The process is normally carried out under normal pressure. However, the cleavage of the thiourea of formula III is preferably carried out under slightly reduced pressure. It is preferred to carry out the cleavage of the thiourea of formula III under a pressure of 0.8 to 1 bar.

The thiourea of formula III can be isolated by filtration or by evaporation of the solvent. After removal of the alkali metal salt or ammonium salt by washing with water, the product is obtained in good purity and in a yield of 95–97% of theory. It is, however, also possible to cleave the thiourea of formula III immediately after its synthesis and after separating the water present in the reaction mixture, without isolation, direct to the isothiocyanate of formula I. The isothiocyanate of formula I can be obtained in simple manner by removing the solvent by distillation and vacuum distillation of the residue.

In a preferred variant of the process of this invention, compounds of formula Ia

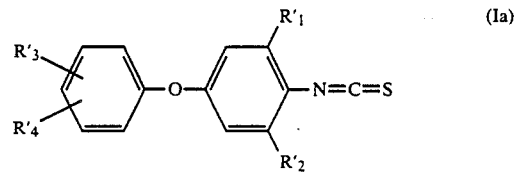

wherein $R'_1$ and $R'_2$ are each isopropyl or sec-butyl, and $R'_3$ is hydrogen, chloro or trifluoromethyl and $R'_4$ is hydrogen or chloro, are prepared by reacting an amine of formula IIa

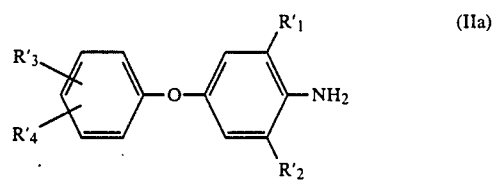

wherein $R'_1$, $R'_2$, $R'_3$ and $R'_4$ are as defined for formula Ia, in the temperature range from 90° to 110° C., in toluene, xylene or a mixture of alkylbenzenes as solvent and in the presence of 1.05 to 1.15 mol of hydrogen chloride per mol of amine of formula IIa, with 1.05 to 1.25 mol of sodium thiocyanate per mol of amine of formula IIa, to the thiourea of formula IIIa

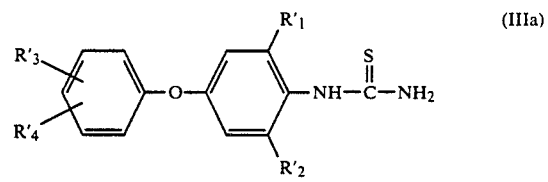

wherein $R'_1$, $R'_2$, $R'_3$ and $R'_4$ are as defined for formula Ia, and cleaving said thiourea of formula IIIa by heating in the temperature range from 140°–160° C., in xylene or a mixture of alkylbenzenes, to the isothiocyanate of formula Ia.

The process of this invention makes it possible to prepare the isothiocyanates of formula I, starting from amines of formula II, in simple manner and in excellent yield, while avoiding the drawbacks of the known processes.

The process of the invention is illustrated with reference to the following Examples.

Example 1: Preparation of N-(4-phenoxy-2,6-diisopropylphenyl)thiourea 305 g (1 mol) of 4-phenoxy-2,6-diisopropylaniline hydrochloride, 97 g (1.2 mol) of sodium thiocyanate, 10 ml of water and 10 ml of concentrated hydrochloric acid are suspended in 800 ml of o-xylene. The mixture is heated to 90° C. over 6 hours, during which time 2 ml of concentrated hydrochloric acid are added after 3 hours and then after each further hour. Thereafter the reaction mixture is cooled to room temperature and the product is isolated by filtration, washed with water and dried, giving 315 g (96% of theory) of N-(4-phenoxy-2,6-diisopropylphenyl)thiourea in the form of pale grey crystals which melt at 219°–221° C.

The starting 4-phenoxy-2,6-diisopropylaniline hydrochloride can be prepared as follows:

With stirring, 21 g (0.15 mol) of potassium carbonate are initially added to 141 g (1.5 mol) of phenol in 500 g of toluene, followed by the addition of 168 g (1.5 mol) of a 50% aqueous solution of potassium hydroxide. The entire water of reaction is then separated under reflux, and then ca. 400 g of toluene are removed by distillation. The residue is dissolved in 700 g of dimethyl formamide. After addition of 6 g (0.05 mol) of copper carbonate, solvent is distilled off until the temperature of the reaction mixture is 140° C. Then 256 g (1 mol) of 4-bromo-2,6-diisopropylaniline are added at 140° C. and the mixture is kept for 10 hours at 140° C. The dimethyl formamide is then removed by vacuum distillation, the residue is extracted with water, and the product is taken up in toluene. After stripping off the toluene, the crude product is purified by vacuum distillation, giving 215 g (80% of theory) of 4-phenoxy-2,6-diisopropylaniline with a boiling point of 142°–145° C./0.04 mbar and a melting point of 69°–71° C., in the form of a bright red product. Conversion to the hydrochloride is effected by dissolving the product in 300 g of butyl acetate, adding 115 g of a 37% solution of hydrochloric acid, and removing the water of reaction by vacuum distillation. The hydrochloride is isolated by filtration, washed with butyl acetate and dried under vacuum, giving 235 g (96% of theory, based on 4-phenoxy-2,6-diisopropylaniline) of 4-phenoxy-2,6-diisopropylaniline hydrochloride in the form of white crystals which melt at 247°–249° C.

Example 2: Preparation of 4-phenoxy-2,6-diisopropylphenylisothiocyanate 315 g (1 mol) of N-(4-phenoxy-2,6-diisopropylphenyl)thiourea are suspended in 800 ml of o-xylene, and the suspension is heated for 5 hours to reflux temperature, whereupon the temperature of the reaction mixture rises to ca. 150° C. The reaction mixture is then cooled, the solvent is removed by vacuum distillation, and the crude product is purified by distillation under a high vacuum, giving 278 g (93% of theory) of 4-phenoxy-2,6-diisopropylphenylisothiocyanate as a pale yellow oil with a boiling point of 130°–140° C./0.05 mbar.

Example 3: Preparation of 4-phenoxy-2,6-diisopropylphenylisothiocyanate 315 g (1 mol) of N-(4-phenoxy-2,6-diisopropylphenyl)thiourea are suspended in 800 ml of Solvesso ® 100 (mixture of alkylbenzenes with a boiling point of 150°–170° C.). The mixture is then heated for 3 hours to 155°–160° C. under a pressure of 800 mbar. The solvent is subsequently removed by distillation under a pressure of 200 mbar, and the residue is purified by distillation under a high vacuum, giving 280 g (94% of theory) of 4-phenoxy-2,6-diisopropylphenylisothiocyanate as a pale yellow oil with a boiling point of 130°–140°/0.05 mbar.

What is claimed is:

1. A process for the preparation of an isothiocyante of formula I

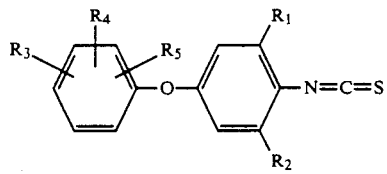

wherein $R_1$ and $R_2$ are each independently of the other $C_1$-$C_6$alkyl and $R_3$, $R_4$ and $R_5$ are each independently of the other hydrogen, halogen, $C_1$-$C_4$alkyl, $C_1$-$C_4$alkoxy, trifluoromethyl or nitro, which process comprises reacting an amine of formula II

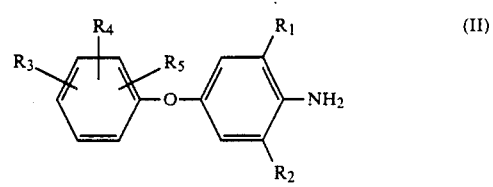

wherein $R_1$, $R_2$, $R_3$, $R_4$ and $R_5$ are as defined for formula I, in the presence of at least the equivalent amount of an acid and in the presence of 0.5–5% by water, based on the total weight of the reaction mixture, in an inert solvent, with ammonium thiocyanate or an alkali metal thiocyanate to a thiourea of formula III

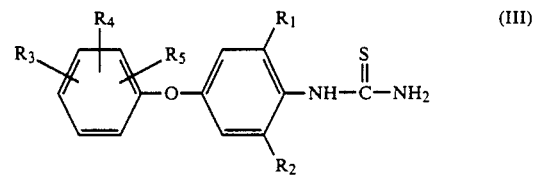

wherein $R_1$, $R_2$, $R_3$, $R_4$ and $R_5$ are as defined for formula I, and cleaving said thiourea by heating to give an isothiocyanate and ammonia.

2. A process according to claim 1, wherein $R_1$ and $R_2$ are each independently of the other $C_2$-$C_4$alkyl, $R_3$ is hydrogen, chloro, methoxy, trifluoromethyl or nitro, and $R_4$ and $R_5$ are each hydrogen or chloro.

3. A process according to claim 1, wherein $R_1$ and $R_2$ are each isopropyl or sec-butyl, $R_3$ is hydrogen, chloro or trifluoromethyl, $R_4$ is hydrogen or chloro, and $R_5$ is hydrogen.

4. A process according to claim 1, wherein $R_1$ and $R_2$ are isopropyl and $R_3$, $R_4$ and $R_5$ are hydrogen.

5. A process according to claim 1, wherein the reaction of the amine of formula II is carried out with ammonium thiocyanate or an alkali metal thiocyanate, in the presence of 1–1.25 equivalents of a strong non-oxidising mineral acid per mol of amine of formula II.

6. A process according to claim 5, wherein 1–1.25 equivalents of hydrochloric acid, hydrobromic acid or sulfuric acid are used per mol of amine of formula II.

7. A process according to claim 5, wherein 1.05–1.15 mol of hydrochloric acid is used per mol of amine of formula II.

8. A process according to claim 1, wherein the amine is used in the form of the hydrochloride.

9. A process according to claim 1, wherein the reaction of an amine of formula II with ammonium thiocyanate or an alkali metal thiocyanate is carried out in an aromatic hydrocarbon or an aliphatic or aromatic halogenated hydrocarbon as solvent.

10. A process according to claim 9, wherein the reaction of an amine of formula II is carried out with ammonium thiocyanate or an alkali metal thiocyanate in toluene, xylene or a mixture of alkylbenzenes as solvent.

11. A process according to claim 9, wherein the reaction of an amine of formula II with ammonium thiocyanate or an alkali metal thiocyanate is carried out in xylene or a mixture of alkylbenzenes having a boiling range from 150° to 170° C.

12. A process according to claim 1, wherein the reaction of the amine of formula II with the ammonium thiocyanate or alkali metal thiocyanate is carried out in the presence of 1–2% by weight of water, based on the total weight of the reaction mixture.

13. A process according to claim 1, wherein the amine of formula II is reacted with sodium thiocyanate.

14. A process according to claim 1, wherein 1.05–1.25 mol of ammonium thiocyanate or alkali metal thiocyanate is used per mol of amine of formula II.

15. A process according to claim 1, wherein the amine of formula II is reacted with the ammonium thiocyanate or alkali metal thiocyanate in the temperature range from 80° to 120° C.

16. A process according to claim 15, wherein the reaction of the amine of formula II with the ammonium thiocyanate or alkali metal thiocyanate is carried out in the temperature range from 90° to 110° C.

17. A process according to claim 1, wherein the thermal cleavage of the thiourea of formula III is carried out in the temperature range from 125° to 170° C.

18. A process according to claim 17, wherein the cleavage of the thiourea of the formula III is carried out in the temperature range from 140° to 160° C.

19. A process according to claim 1, wherein the cleavage of the thiourea of formula III is carried out under a pressure of 0.8–1 bar.

20. A process for the preparation of a compound of formula Ia

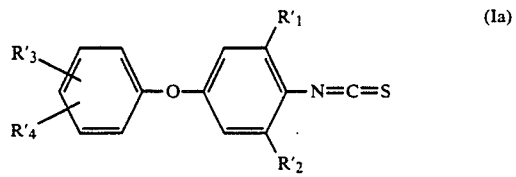

wherein $R'_1$ and $R'_2$ are each isopropyl or sec-butyl, $R'_3$ is hydrogen, chloro or trifluoromethyl and $R'_4$ is hydrogen or chloro, which comprises reacting an amine of formula IIa

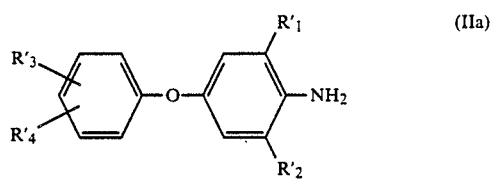

wherein $R'_1$, $R'_2$, $R'_3$ and $R'_4$ are as defined for formula Ia, in the temperature range from 80° to 90° C., in toluene, xylene or a mixture of alkylbenzenes as solvent, and in the presence of 1.05 to 1.15 mol of hydrogen chloride per mol of amine of formula IIa, with 1.05 to 1–25 mol of sodium thiocyanate per mol of amine of formula IIa, to the thiourea of formula IIIa

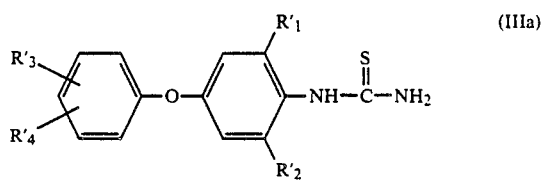

wherein $R'_1$, $R'_2$, $R'_3$ and $R'_4$ are as defined for formula Ia, and cleaving said thiourea of formula IIIa by heating in the temperature range from 140°–160° C., in xylene or a mixture of alkylbenzenes, to the isothiocyanate of formula Ia.

* * * * *